United States Patent [19]

Hentschel et al.

[11] 4,271,298

[45] * Jun. 2, 1981

[54] PROCESS FOR THE PRODUCTION OF SUSPENSIONS OR SOLUTIONS OF CYANURIC CHLORIDE IN WATER

[75] Inventors: Klaus Hentschel, Kalmthout, Belgium; Friedrich Bittner, Bad Soden; Gerd Sohreyer, Hanau, both of Fed. Rep. of Germany

[73] Assignee: Deutsche Gold- und Silber-Scheideanstalt vormals Roessler, Frankfurt, Fed. Rep. of Germany

[ * ] Notice: The portion of the term of this patent subsequent to Jun. 2, 1998, has been disclaimed.

[21] Appl. No.: 94,875

[22] Filed: Nov. 16, 1979

[30] Foreign Application Priority Data

Nov. 20, 1978 [DE] Fed. Rep. of Germany ....... 2850242

[51] Int. Cl.$^3$ .......................................... C07D 251/28
[52] U.S. Cl. .................................................. 544/190
[58] Field of Search ........................................ 544/190

[56] References Cited

U.S. PATENT DOCUMENTS 3,256,070  6/1966  Trickey .................................. 23/294
3,925,377  12/1975  Geiger et al. ........................ 260/248

FOREIGN PATENT DOCUMENTS 1545840 10/1969 Fed. Rep. of Germany .
1670731 12/1970 Fed. Rep. of Germany .
2332636 1/1975 Fed. Rep. of Germany .

OTHER PUBLICATIONS

Ullmann, Enzyklopadie der technischen Chemie, 3rd Ed. (1954), vol. 1, pp. 743-744; 769-770
Ibid, vol. 5, pp. 624-625.

Primary Examiner—John M. Ford
Attorney, Agent, or Firm—Cushman, Darby & Cushman

[57] ABSTRACT

Suspension or solutions of cyanuric chloride in water are prepared at high mixing velocities and low temperatures with resulting low degree of hydrolysis by introducing liquid cyanuric chloride through a nozzle in the upper portion of the mixing apparatus in countercurrent flow to upwardly flowing water introduced from at least one lower nozzle above a breast shaped constriction in the lower, open portion of the apparatus. In this way the chamber walls are always covered with an unbroken layer of liquid. The process can be carried out at normal, reduced or elevated pressure. At reduced pressure by evaporation of the water there is simultaneously a cooling of the system.

4 Claims, 3 Drawing Figures

PROCESS FOR THE PRODUCTION OF SUSPENSIONS OR SOLUTIONS OF CYANURIC CHLORIDE IN WATER

BACKGROUND OF THE INVENTION

Cyanuric chloride which is produced by the trimerization of cyanogen chloride with the help of catalysts, above all activated carbon, as is known is a very interesting intermediate produce in various industrial sectors such as the production of dyestuffs and products for the textile industry, as well as for pharmaceuticals, products for agriculture, as well as for the synthetic resin, rubber and explosive industries.

As is known after the trimerization cyanuric chloride is obtained in gaseous form, together with unreacted cyanogen chloride and chlorine, as well as byproducts.

For a long time it was customary to convert this gaseous reaction mixture directly into solid-cyanuric chloride, e.g. by leading the gaseous mixture into a chamber cooled from outside (see Ullmann, Enzyklopä die der technischen Chemie, 3rd edition, 1954 Vol. 5, pages 624–625 and 4th edition, 1975 Vol. 9, pages 652), or by introducing it into a ball mill cooled with water according to the process of Trickey U.S. Pat. No. 3,256,070.

Solid cyanuric chloride generally is obtained in powder form and until now has been further processed predominantly in this form.

In order to increase its reaction velocity in the further processing it is desirable to have the cyanuric chloride present either in finely divided or dissolved form.

Since cyanuric chloride at all temperatures is virtually insoluble in pure water, it can only be obtained in water in the form of suspensions.

In most cases previously cyanuric chloride was suspended as a solid in water. In so doing there occurs to be sure a slight degree of hydrolysis since cyanuric chloride, as mentioned, is barely osluble in neutral water.

Solid cyanuric chloride, however, frequently contains small amounts of chlorine and cyanogen chloride which form with water through disproportionation or saponification byproducts, above all hydrochloric acid.

The previously neutral water becomes more or less strongly acidic according to the content of chlorine and cyanogen chloride.

However, in acidic aqueous solutions the hydrolysis begins to become greater.

Particularly in the continuous processing of aqueous suspensions it has been established that the degree of hydrolysis of cyanuric chloride increases with the size of the deposition container, i.e., the longer the residence time of the suspension or a portion of it in this container before it is withdrawn the more strongly is the hydrolysis.

These disadvantages which occur in the production of cyanuric chloride suspension in water should be eliminated by using molten cyanuric chloride which is permitted to run into water, see Wojahn German patent No. 1670731 and related Wojahn U.S. Pat. No. 3,575,880.

The molten cyanuric chloride through the previous melting process has lost a portion of the chlorine and cyanogen chloride adhering to the solid cyanuric chloride, which reduces the danger of hydrolysis.

Depending on the mixing ratio of molten cyanuric chloride and water the mixing temperature can assume a considerable value, because of which even with small amount of chlorine can initiate a hydrolysis.

Thus, according to the data in the mentioned patent, at a mixing ratio of water to cyanuric chloride of 4:1 the mixing temperature of the aqueous suspension is almost 50° C., if water of 20° C. is added in order to produce a suspension from the cyanuric chloride melt. At lower mixing ratios the mixing temperature was even far higher.

Higher mixing ratios than 4:1 according to the data of the mentioned patent do not result in a considerable reduction of the mixing temperature since this approaches a limiting value which is using water at 20° C. lies at about 45° C.

Since the apparatus employed only can be operated at normal pressure, it was not possible to simultaneously lower the temperature by lowering the pressure and therewith set up lower mixing temperatures.

Additionally the suspensions obtained by the process of German patent No. 1670731 were too large grained for later uses and after their production first must be communicated, e.g., in wet milling, also in using a nozzle.

The object of the invention therefore is the production of fine particle cyanuric chloride suspensions in water with a very small degree of hydrolysis of the cyanuric chloride.

SUMMARY OF THE INVENTION

Figure 1:
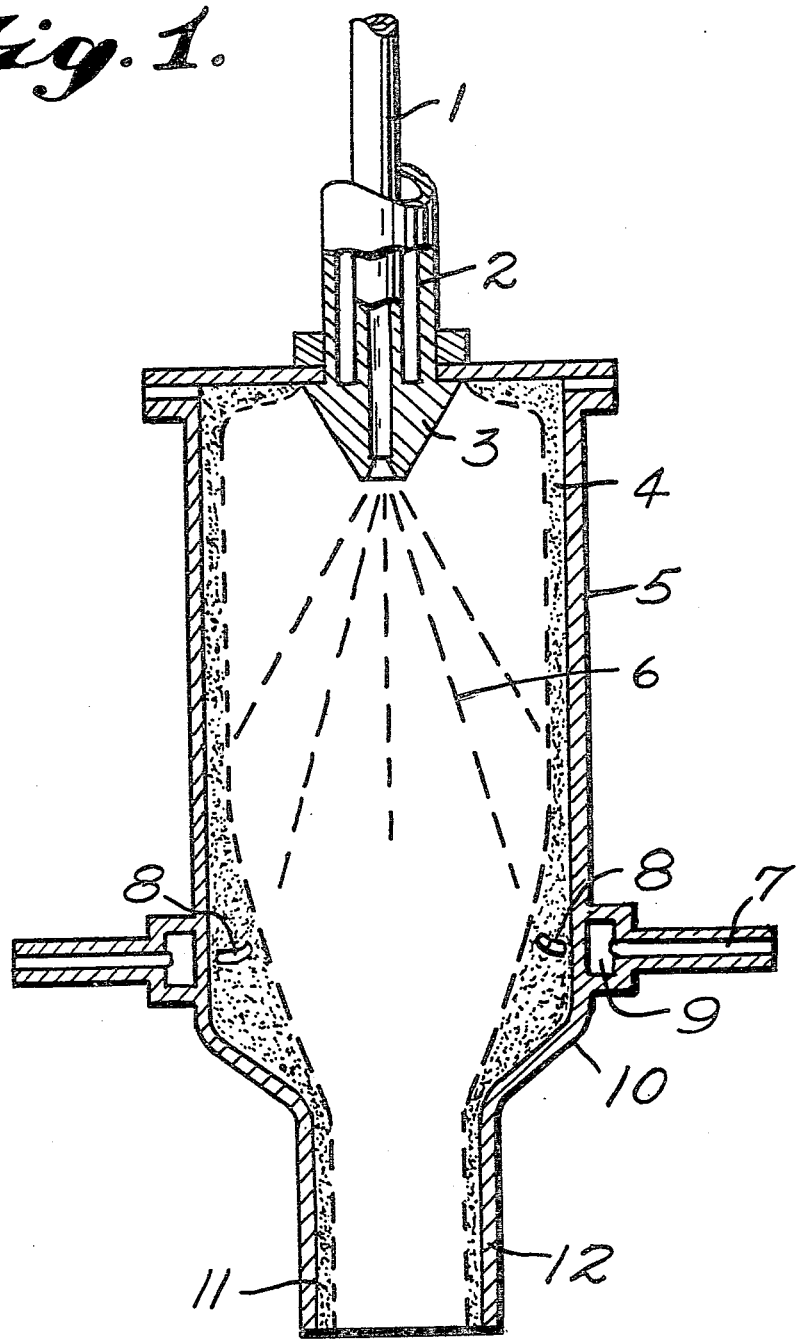
FIG. 1 is a vertical sectional elevation of one form of apparatus suitable for carrying out the process of the invention.

It has now been found that suspensions or solutions of cyanuric chloride can be produced while avoiding or very greatly reducing the hydrolysis of cyanuric chloride by bringing into contact liquid cyanuric chloride and water with the help of a nozzle if liquid cyanuric chloride which is preferably free from chlorine and cyanogen chloride is sprayed into a container at temperatures in its molten range, if necessary in the presence of an inert gas, through a nozzle, preferably a spray nozzle, which is located in the head of a tubular container, during which this tubular container is closed or closeable at the top and downwardly constricted breast shaped to a discharge opening and with which the water discharges through one or preferably several nozzles, preferably polished steel nozzles, which are located above the constriction and consist of one or more tangential spray agencies arranged in one or more rows which are arranged slightly above in the direction of the upper closing device or are arranged in the direction of the nozzle located in the upper portion and form a liquid layer along the entire chamber walls up to the nozzle for the cyanuric chloride, whereby the thickness of this layer at the breast shaped restriction is greater than at the rest of the chamber walls, and in which the sprayed cyanuric chloride enters.

The liquid cyanuric chloride is preferably introduced into the nozzle through a heated conduit.

By using the described apparatus it is possible to so distribute the water at the chamber walls that the liquid layer at the breast shaped constriction is thicker than at the remaining chamber walls.

By the expression used in the glass art: "breast shaped constriction" is meant a constriction which does not proceed steeply, but in a flat S curve going from the wall of the tubular container to the discharge opening. Corresponding constrictions are also present in red wine bottles at the transition from the true bottle to the neck.

The constriction in the tubular container can preferably always begin where about 50% of the sprayed particles meet the liquid layer built up on the wall. Preferably this is the case in the lower third of the tubular container.

The size of the diameter of the discharge opening of itself is not critical. Naturally it depends on the viscosity of the medium being discharged and must have at least such a size that air can enter.

The discharge opening is preferably converted into a discharge tube which has any desired diameter, preferably however, the same diameter or larger than the discharge opening.

The nozzle or nozzles for the water to be sure can be arranged at any place in the tubular container above the constriction, but preferably are located in the region directly above the breast shaped constriction.

As the tangentially arranged spray agencies, there can be used small tubes or nozzles as well as openings in the chamber walls or, with the presence of a feed ring, in its chamber walls.

Preferably there are used small tubes.

The tubular container described has the great advantage that it can be operated not only at an atmospheric pressure but also at reduced pressure. Thus without doing anything further it permits the adjustment proceeding from atmospheric pressure to reduce pressure of 0.01 bar.

At reduced pressure a portion of the water evaporates through which a cooling of the solution or suspension forming takes place. The mixing temperature in this way lets itself be held readily to a low level which is very essential for a continuous procedure.

The mixing temperature arising according to the process of the invention generally are in the range of 10 to 15° C. although this can be varied.

The mixing temperature naturally depends on both the mixing ratio "water cyanuric chloride melt" which generally is in the range of 6:1 to 1:1.

A suitable apparatus for the recovery of the mentioned cyanuric chloride suspensions or solutions is described and claimed in U.S. Hentschel application Ser. No. 94,803, filed Nov. 15, 1979 and entitled "Apparatus For Bringing Liquids In Contact" which is operated in the following manner.

As shown in FIG. 1 the liquid cyanuric chloride in supply line 1 is led through a coaxial heater 2 via a unary or binary nozzle 3 into the mixing chamber 5, i.e., the tubular container 5.

When using only one supply and only one spray organ, e.g. opening into the mixing chamber 5, the supply 7 passes directly into the spray opening 8 and the segmented chamber 9 is eliminated.

Besides the component in the circumferential direction the water jet has a velocity component in the axial direction. Therethrough the liquid reaches the wall of the mixing chamber 5. There it builds a liquid layer 4.

The cyanuric chloride leaving the nozzle 3 is sprayed into the liquid layer 4. The spray angle for the cyanuric chloride sprayed out of nozzle 3 can be between 15° and 150° preferably between 15° and 120°.

The shape of the spray varies from hollow or solid cone up to an unarranged mist, according to the type of nozzle.

Upon entering the spray particles 6 solidify and/or the sprayed cyanuric chloride dissolves in the liquid layer. The energy brought in is given up to the liquid layer, independent of the pressure in the tubular container.

The discharging mixture which leaves the tubular container 5 through the discharge opening 12 goes to the container 14 which can be connected if desired detachably, either directly or indirectly via line 13 to the discharge opening 12 of the container 5.

Figure 3:
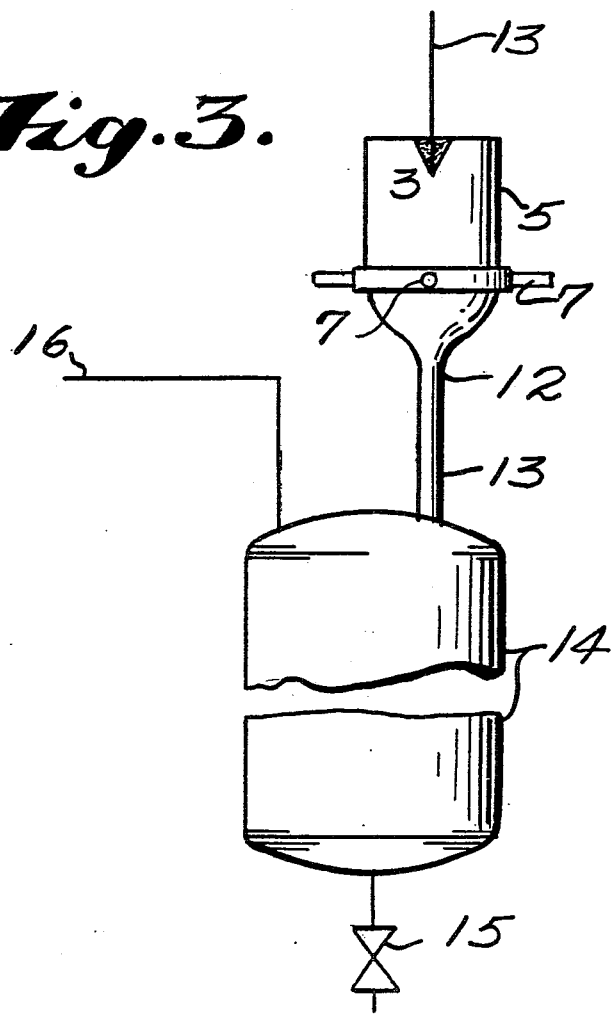
FIG. 3 is a schematic view of apparatus for carrying out the invention.

In this way it is possible to establish any desired pressure, i.e., any reduced or excess pressure, in the tubular container 5 and container 14 through known apparatus which is connected with the container 14 via line 16, see FIG. 3. (However, the known apparatuses for regulating the pressure are not shown in FIG. 3.)

The mixture is withdrawn at the discharge valve 15. The container 14, however, can in a given case also serve as reaction container for a further treatment or reaction.

However, it is also possible to apply reduced or superatmospheric pressure directly into the discharge line 13 through the known apparatuses and to transport away in known manner the discharging mixture from line 13 while eliminating an intermediate connection from container 14.

The apparatuses 5 and 14 shown in FIGS. 1 and 3, in a given case also line 13, can be heated or cooled in known manner, according to the requirements, see e.g., Ullmann, Enzyklopädie der technischen Chemie, Vol. 1, 3rd edition, 1951, pages 743–744 and 769–770.

Likewise there can be used for this purpose the known construction materials, loc. cit.

The volume of the tubular container 5 is determined by the properties of the liquid used whereby the path of the sprayed particles 6 up to the impingment on the liquid layer 4 should be held as short as possible.

Through this it is possible to carry out relatively large throughputs in a very small tubular container, e.g. the volume in Example 3 is about 1.2 liters. By establishing a specific pressure, e.g., a reduced pressure in mixing chamber 5, the heat energy of the sprayed cyanuric chloride in contact with the liquid layer can be removed.

The suspension or solution of cyanuric chloride and water produced leaves the mixing chamber through the discharge 12.

To improve the formation of the water layer the spray systems 8 tangential to the mixing chamber are directed slightly upwardly. The exact angle of bending is so adjusted that the liquid layer reaches up to the nozzle, but does not touch it.

Through the breast shaped constriction and the thicker liquid layer produced at this wall position thereby there results, despite the outlet opening, that the remaining chamber walls always are covered with a uniform, i.e. uninterrupted layer of water. Through this there is guaranteed a high mixing velocity which can be increased by bringing a gas in with the water.

The spray cone of the liquid cyanuric chloride is designated by the number 6.

The number of inlet lines 7 depends on the particular case.

Figure 2:
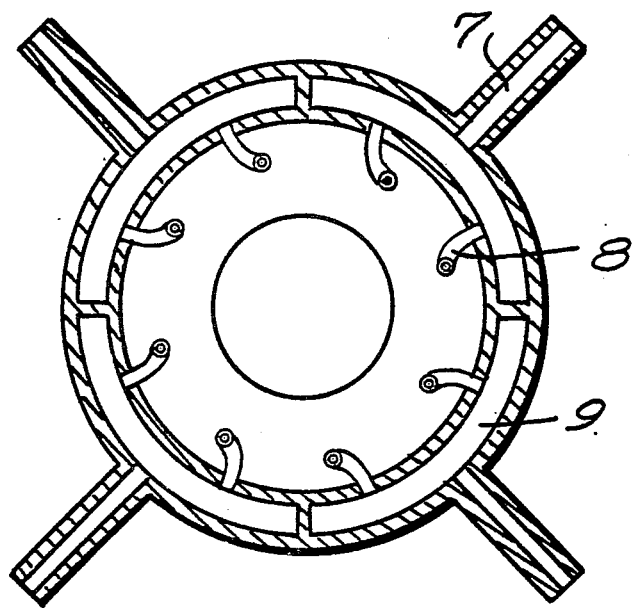
FIG. 2 is a cross-sectional view along the line 2—2 of FIG. 1.

Thus in feeding in the water one supply line is sufficient, however, for better distribution of the water there has also proven as desirable to use several supply lines, see for example FIG. 2.

Liquid cyanuric chloride can be obtained according to known process, e.g. according to Geiger, German patent No. 2,322,636 and related Geiger U.S. Pat. No. 3,925,377. The entire disclosure of the Geiger U.S. patent is hereby incorporated by reference and relied upon.

Preferably according to the process of the invention there is employed a liquid cyanuric chloride whose temperature is 170° C. and which is free from chlorine and cyanogen chloride. For freeing from chlorine and cyanogen chloride known processes are suitable, as e.g. dephlegmatization.

The suspensions and solutions of cyanuric chloride produced according to the invention in leaving the apparatus have a very slight degree of hydrolysis since the residence times and recovery temperatures can be held very low.

These kinds of suspensions or solutions at the temperatures with which they leave the apparatus can be stored up to hours.

The resulting suspensions besides are very fine-grained, any formation of clumps is avoided.

In this way, there can be produced at will suspensions or solutions of cyanuric chloride continuously according to the requirements of the moment.

Unless otherwise indicated all parts and percentages are by weight.

The process can comprise, consist essentially of or consist of the steps set forth and the materials can comprise, consist essentially of or consist of those set forth.

The invention will be further explained through the following examples.

DESCRIPTION OF THE PREFERRED EMBODIMENTS

EXAMPLE 1

Liquid cyanuric chloride at about 170° C. is led via the heated supply line 1 into the unary nozzle 3. The nozzle 3 has a bore of 1.54 mm and a spray angle of about 78°. The supply pressure of the liquid cyanuric chloride was 5.9 bar. There were sprayed 80.5 kg/h of cyanuric chloride through the nozzle 3 into the mixing chamber 5. The mixing chamber 5 had a diameter of 100 mm and atmospheric pressure prevailed in it. Water (966 kg/h) via 4 different supply lines 7 arrived at the chamber segments 9 and after leaving from light small tubes 8 formed a liquid layer 4 in the mixing chamber 5.

The suspension of cyanuric chloride and water left the mixing chamber 5 through the pipe 12. The concentration of cyanuric chloride in the suspension was 7.7%.

The value of the Simazin test, (see Ullmann, Enzyklopädie der technischen Chemie, 4th edition, 1975, Vol. 9, page 652), a measure for the reactability of cyanuric chloride was 55 min. and 0.6% residue. The ASS test (Ullmann, Vol. 9, page 652) produced a residue of 0.6%.

EXAMPLE 2

The experimental conditions were changed compared to Example 1 as follows:
The bore of the cyanuric chloride nozzle 1.1 mm.
The spray supply pressure 6.0 bar.
The amount of cyanuric chloride 40.5 kg/h.
The pressure in the mixing chamber 0.13 bar and the resulting cyanuric chloride concentration in water was 4.0%.

The value of the Simazin test was 55 min. and 0.2% residue. The ASS test produced a residue of 0.5%.

EXAMPLE 3

The experimental conditions were changed compared to Example 1 as follows:
The bore of the cyanuric chloride nozzle 1.85 mm.
The spray supply pressure 6.0 bar.
The amount of cyanuric chloride 118 kg/h and the resulting cyanuric chloride concentration in water was 10.9%.

The value of the Simazin test was 45 min. and 0% residue. The ASS test produced a residue of 0.3%.

EXAMPLE 4

The experimental conditions were changed compared to Example 1 as follows:
The bore of the cyanuric chloride nozzle 1.17 mm.
The spray angle of the nozzle about 70°.
The amount of cyanuric chloride 30.6 kg/h.
The amount of water 555 kg/h.
The chamber diameter 80 mm. and the resulting cyanuric chloride concentration in water was 5.2%.

The value of the Simazin test was 37 min. and 0% residue. The ASS test produced no residue.

The particle spectrum of the cyanuric chloride particles produced in Example 1-4 on the average had the following appearance.
>100 microns: 3%
>63 microns: 14%
>40 microns: 33%
>10 microns: 50%
<10 microns: 50%

What is claimed is:

1. A process for the production of a suspension or solution of cyanuric chloride in water comprising spraying cyanuric chloride downwardly and outwardly at a temperature in its molten range from upper portion of a vertical tubular zone closed at the top thereof to contact and mix with said water which forms a liquid layer defining said tubular zone, constricting said layer in breast-shaped manner downwardly below the place of entry of the cyanuric chloride into the tubular zone to form a narrower discharge opening, discharging said water as a spray tangentially to said layer and directed slightly upwardly in the direction of the closed top above said constriction and below the point of introduction of the cyanuric chloride and thereby forming said liquid layer along the entire tubular zone to the point of introduction of the cyanuric chloride, whereby the thickness of said layer where it is formed in the breast-shaped constriction is greater than it is in the remainder of the tubular zone.

2. The process of claim 1 wherein the liquid cyanuric chloride employed is free from chlorine or cyanogen chloride.

3. The process of claim 1 including reducing the pressure to between below atmospheric pressure and 0.01 bar and thereby lowering the mixing temperature.

4. A process according to claim 1 comprising discharging the solution or suspension formed to another container adapted for use at subatmospheric or superatmospheric pressure.

* * * * *